US008609697B2

(12) United States Patent
Beilfuss et al.

(10) Patent No.: US 8,609,697 B2
(45) Date of Patent: Dec. 17, 2013

(54) STABILIZED, ANTIMICROBIALLY EFFECTIVE COMPOSITION WITH A CONTENT OF BISPYRIDINIUM ALKANE

(75) Inventors: Wolfgang Beilfuss, Hamburg (DE); Andreas Dettmann, Hamburg (DE); Sabine Behrends, Appen (DE); Mona Golombiewski, Luneburg (DE); Thomas Spuida, Hamburg (DE); Elke Kassens, Grabau (DE)

(73) Assignee: Air Liquide Sante (International), Paris (FR)

( * ) Notice: Subject to any disclaimer, the term of this patent is extended or adjusted under 35 U.S.C. 154(b) by 133 days.

(21) Appl. No.: 12/919,523

(22) PCT Filed: Feb. 18, 2009

(86) PCT No.: PCT/EP2009/051927
§ 371 (c)(1),
(2), (4) Date: Aug. 26, 2010

(87) PCT Pub. No.: WO2009/106467
PCT Pub. Date: Sep. 3, 2009

(65) Prior Publication Data
US 2011/0003857 A1    Jan. 6, 2011

(30) Foreign Application Priority Data
Feb. 28, 2008  (DE) .......... 10 2008 011 691

(51) Int. Cl.
*A01N 43/40* (2006.01)
*A61K 31/4425* (2006.01)

(52) U.S. Cl.
USPC ..... 514/332; 514/334; 424/70.31; 424/70.28; 424/417

(58) Field of Classification Search
USPC ............ 514/332, 334; 424/70.28, 70.31, 417
See application file for complete search history.

(56) References Cited

U.S. PATENT DOCUMENTS

| 4,420,484 A | 12/1983 | Gorman et al. |
| 4,900,721 A | 2/1990 | Bansemir et al. |
| 4,992,259 A * | 2/1991 | Schiraldi et al. ........ 424/49 |
| 2001/0036963 A1 | 11/2001 | Behrends et al. |
| 2005/0119313 A1 | 6/2005 | Behrends et al. |

FOREIGN PATENT DOCUMENTS

| DE | 27 08 331 A1 | 9/1977 |
| DE | 42 01 391 A1 | 7/1993 |
| DE | 102 05 883 A1 | 8/2003 |
| DE | 10 2005 045146 A1 | 3/2007 |
| EP | 0 252 278 A2 | 1/1988 |
| EP | 0 494 057 A1 | 7/1992 |
| GB | 2 317 339 A | 3/1998 |
| WO | 02/02128 A2 | 1/2002 |
| WO | 03/067988 A1 | 8/2003 |
| WO | 2006/069210 A2 | 6/2006 |
| WO | WO2007031519 * | 3/2007 ......... A01N 43/42 |
| WO | 2008/052912 A1 | 5/2008 |

OTHER PUBLICATIONS

Product insert for Plantacare 1200 2004, downloaded from the internet on Jun. 7, 2012, URL: http://www.bsibusiness.com/uploads/product/pdf/289_pdf.pdf.*
Royack et al. (Oral oncology, 36, 2000, pp. 37-41).*
International Search Report, dated Jul. 19, 2010, from corresponding PCT application.
German Office Action, dated May 15, 2008, from corresponding German application.
Schick, M.J. [Ed.]: Nonionic Surfactants—Physical Chemistry, 1987, Surfactant Science Series, vol. 23, pp. 1011-1072, New York [etc.]; Marcel Dekker, ISBN: 0-8247-7530-9.
German Office Action, dated Apr. 11, 2011.

* cited by examiner

*Primary Examiner* — Savitha Rao
(74) *Attorney, Agent, or Firm* — Young & Thompson

(57) ABSTRACT

An aqueous-based composition which includes a) at least one bispyridinium alkane (for example octenidine) and b) at least one stabilizer selected from antioxidants, complexing agents, reducing agents, UV filters and photoprotective agents, in particular α-tocopherol, and BHT. The composition can also include c) one or more auxiliaries selected from, for example, nonionic surfactants, ethers, solvents and polymers, in particular fatty alcohol alkoxylates and alkoxylated fatty acid monoglycerides. The presence of the stabilizer reduces or prevents the appearance of decomposition products of bispyridinium alkanes and, in the case of the presence of auxiliaries, of decomposition products of the auxiliaries, such as ethers and peroxides.

6 Claims, No Drawings

STABILIZED, ANTIMICROBIALLY EFFECTIVE COMPOSITION WITH A CONTENT OF BISPYRIDINIUM ALKANE

The present invention relates to a stabilized, antimicrobially effective aqueous-based composition which comprises a bispyridinium alkane, and to the use of the composition for producing microbicidally effective cosmetic and pharmaceutical preparations and also for producing microbicidally finished articles such as medicinal products and biocidal products such as disinfectants and antimicrobial cleaners. The composition can be used as raw material, concentrate or ready-to-use product for the stated applications.

Compositions and preparations with a content of bispyridinium alkane (for example N,N'-(1,10-decanediyldi-1-[4H]-pyridinyl-4-ylidine)bis(1-octanamine)dihydrochloride (octenidine below)) are known. Octenidine is a bispyridinium alkane with the following mesomeric limiting structures:

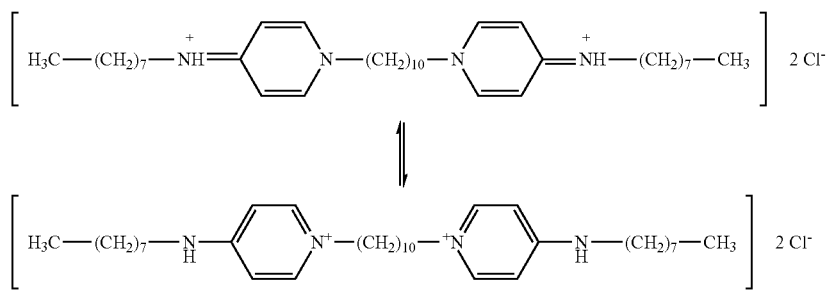

Applications of such compositions and preparations are in the field of antisepticising skin, mucosa, wounds or internal organs and also as bacteriostatic agent and agent for removing dental plaque. Octenidine has been successfully used for years, inter alia, in the mucosa and wound antiseptic Octenisept® from Schülke & Mayr GmbH, Norderstedt, Germany.

Surprisingly, it has now emerged that formulations which comprise bispyridinium alkane have a tendency towards decomposition upon prolonged (e.g. several months') storage. This decomposition arises in particular in the case of specific formulations which comprise especially octenidine and optionally specific auxiliaries. Thus, in experiments in connection with the present invention, it has been established that degradation products of octenidine and, in the case of the use of octenidine in combination with certain auxiliaries, also peroxides and aldehydes can form. This was completely surprising against the background of the fact that bispyridinium alkanes such as octenidine were hitherto not known to be unstable. It was surprising in particular that the hitherto unknown instability of bispyridinium alkanes is further increased in the presence of auxiliaries. The conditions which can exert an unfavourable influence on the stability of bispyridinium alkane and—if present of the specific auxiliaries include relatively high temperatures or thermal stress, the effect of light (e.g. sunlight, UV radiation) and other types of electromagnetic radiation.

The object of the invention is accordingly to overcome this problem and to find stabilizers for bispyridinium alkanes. The stabilizers should be effective in a small amount and toxicologically acceptable and reduce or prevent the appearance of decomposition products of bispyridinium alkane, of peroxides and of aldehydes, in particular in the presence of auxiliaries.

It has now surprisingly been found that this object is achieved by an aqueous-based composition which comprises:
a) at least one bispyridinium alkane and
b) at least one stabilizer selected from antioxidants, complexing agents, reducing agents, UV filters, photoprotective agents or combinations of these substances.

Further optional constituents are further microbicidal active ingredients, functional additives or additional ingredients such as wetting agents, solvents, emulsifiers, cleaning components and osmolytes. In one preferred embodiment, further optional constituents are:
c) auxiliary,
d) fruit acid and/or salts thereof,
e) aroma and/or sweetener
and/or
f) acid, base and/or buffer.

Preferred embodiments of the invention are the subject of the dependent claims.

The invention is based inter alia on the fact that it has been found that by using special stabilizers, the decomposition of bispyridinium alkanes in particular octenidine, which occurs under the aforementioned conditions, is reduced or even prevented. Furthermore, the addition of the stabilizers reduces the appearance of a neck-in effect in the case of packs with preparations containing bispyridinium alkanes, in particular octenidine-containing preparations. Moreover, the appearance of discolourations, the formation of odiferously and/or toxicologically undesired components and the appearance of inhomogeneities such as precipitates are suppressed.

a) Bispyridinium Alkane

Compositions according to the invention comprise at least one bispyridinium alkane. The term bispyridinium alkane includes the bis[4-(substituted-amino)-1-pyridinium]alkanes disclosed in DE 27 08 331 C2 and DE 102 05 883 A1. Whereas all details relating to bispyridinium alkanes apply to the entire substance class, they apply in particular to octenidine, which is preferred in all embodiments of the invention.

Thus, octenidine is particularly preferably used as component a).

Preferred concentrations of component a) are 0.0001 to 99.95% by weight, preferably 0.01 to 20% by weight, more preferably 0.05 to 10% by weight, in particular 0.1 to 1.0% by weight, for example about 1.0% by weight or about 0.1% by weight.

b) Stabilizer

Compositions according to the invention comprise at least one stabilizer selected from antioxidants, complexing agents, reducing agents, UV filters (organic or inorganic such as ZnO, TiO$_2$), photoprotective agents or combinations of these substances.

Antioxidants which are effective according to the invention as stabilizers for bispyridinium alkanes are acetylcysteine, 3-tert-butyl-4-hydroxyanisole, 2,6-di-tert-butyl-p-cresol, tert-butylhydroquinone, caffeic acid, chlorogenic acid, cysteine, cysteine hydrochloride, decyl-mercaptomethylimidazole, diamylhydroquinone, di-tert-butylhydroquinone, dicetyl thiodipropionate, digalloyl trioleate, dilauryl thiodipropionate, dimyristyl thiodipropionate, dioleyltocopherylmethylsilanol, disodium rutinyldisulphate, distearyl thiodipropionate, ditridecyl thiodipropionate, dodecyl gallate, erythorbic acid, ethyl ferulate, ferulic acid, hydroquinone, p-hydroxyanisole, hydroxylamine hydrochloride, hydroxylamine sulphate, isooctyl thioglycolate, kojic acid, madecassicoside, methoxy-PEG-7-rutinyl succinate, nordihydroguaiaretic acid, octyl gallate, phenylthioglycolic acid, phloroglucinol, propyl gallate, rosmarinic acid, rutin, sodium erythorbate, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, tocopherol (e.g. vitamin E) and its derivatives (e.g. vitamin E derivatives such as vitamin E acetate, vitamin E linoleate, vitamin E nicotinate and vitamin E succinate), o-tolylbiguanide, tris(nonylphenyl) phosphite, dexpanthenol, alpha-hydroxycarboxylic acids (e.g. glycolic acid, lactic acid, mandelic acid) and salts thereof, p-hydroxybenzoic acid esters (e.g. its methyl, ethyl, propyl or butyl esters), dimethyloldimethylhydantoin, N-acylamino acids and salts thereof (e.g. N-octanoylglycine, Lipacide C8G), ascorbic acid and hinoktiol.

The tocopherols are particularly effective antioxidants according to the invention. Furthermore, with regard to the applications of the compositions according to the invention, which are associated with strict legal regulations and toxicity tests, the tocopherols are particularly desirable antioxidants in the production of cosmetics and pharmaceuticals.

Tocopherols occur in vegetable oils; the seed oils from soya, wheat, corn, rice, cotton, lucerne and nuts, fruits and vegetables such as raspberries, peas and beans, fennel, paprika and celery are particularly rich in tocopherols.

The physiological effect of the tocopherols is based on their properties as free-radical scavengers. Thus, the tocopherols, when they are used according to the invention as antioxidants and thus also find their way, in small amounts, into the preparations furnished with bispyridinium alkane, can for their part even act as physiologically effective antioxidants in the cell membrane and in lipoproteins. Alpha-tocopherol (vitamin E, anti-sterility factor) is the most physiologically effective and most widespread natural tocopherol.

Although the tocopherols used may be of synthetic origin, it is possible to use tocopherols of natural origin. It is possible to use sterically uniform enantiomers or enantiomer mixtures of tocopherols, accordingly for the derivatization to acetate, succinate, linoleate and nicotinate, tocopherols of natural and/or synthetic origin and sterically uniform enantiomers or mixtures of tocopherols (in particular alpha-tocopherol) can be used.

Stabilizers used according to the invention are preferably selected from α-tocopherol, 2,6-di-tert-butyl-4-methylphenol (BHT), tocopherol acetate, 2-tert-butyl-4-hydroxyanisole and/or 3-tert-butyl-4-hydroxyanisole (BHA), dodecyl gallate and ascorbic acid. Preferred stabilizers are vitamin E, BHA, BHT or alkyl gallate or combinations of these substances, in particular α-tocopherol and BHT.

In this connection, a preferred amount of component b) is 0.0001 to 2% by weight, for example 0.002 to 1.0% by weight, such as 0.005 to 0.5% by weight.

c) Auxiliary

The composition according to the invention optionally comprises at least one auxiliary selected from atmospheric oxygen, oxygen-releasing compounds, ozone, oxidizing agents, heavy metal salts (in particular in relatively high oxidation states), impurities (e.g. technically unavoidable impurities) in substances such as metal salts (e.g. heavy metal salts), polymerization initiators, free-radical formers, peroxides, photosensitizers, enzymes, peptides, polymers, solvents, ethers and surfactants such as nonionic surfactants. In one preferred embodiment, the composition according to the invention optionally comprises one or more auxiliary(ies) selected from nonionic surfactants, ethers, solvents and polymers.

The invention is based inter alia on the fact that it has surprisingly been found that certain constituents which are referred to here as auxiliaries, decompose in combination with a) bispyridinium alkane and in some cases even promote the decomposition of bispyridinium alkane, and that this decomposition is prevented or at least reduced in the presence of the stabilizers b) according to the invention.

Preferred nonionic surfactants which are used as auxiliaries b) in compositions according to the invention are selected from fatty alcohol polyalkoxylates, sorbitan fatty acid esters and polyoxyethylene sorbitan fatty acid esters, alkyl glycosides and alkoxylated (in particular ethoxylated) fatty acid monoglycerides, where fatty acid monoglyceride substituted with 5 to 100 ethoxy groups is preferred, in particular fatty acid monoglyceride substituted with 20 to 70 ethoxy groups, such as, for example, with about 40 ethoxy groups (i.e. macrogol glycerol hydroxystearate with 40 ethylene oxide units, which is available under the names Eumulgin HRE 40 PH® from Cognis and Cremophor RH 40® from BASF).

The alcohol polyalkoxylates also include fatty alcohol alkoxylates, e.g. isodecyl ethoxylates with varying fractions of ethylene oxide, isotridecyl ethoxylates, polyethylene glycol ethers of stearyl, lauryl and cetyl and oleyl alcohol. Here, the alcohols may have been alkoxylated with ethylene oxide, propylene oxide or any desired mixtures of ethylene oxide and propylene oxide. Alcohol polyalkoxylates are known, inter alia, under the names Lutensol®, Marlipal®, Marlox®, Brij® and Plurafac®, with Brij35 (macrogol lauryl ether 20-23) being preferred.

Furthermore, the nonionic surfactants used are the sorbitan esters mostly present as oleates, stearates, laurates and palmitates, which are referred to as polysorbates (e.g. Tween®).

Furthermore, the nonionic surfactants used are alkyl glycosides.

Furthermore, the following solvents are used as auxiliaries b): polyalkylene glycols, such as polyethylene glycol, polypropylene glycol, alkylene glycol ethers, such as phenoxyethanol, phenoxypropanols, aromatic alcohols, such as benzyl alcohol, and glycerol ethers such as Sensiva SC 50 and propylene glycol and glycerol. Preferably, solvents with pharmaceutical grade features are used.

Here, a preferred amount of component c) is 0.01 ppm to 99.99% by weight, such as 0.1 to 20% by weight, preferably 0.5 to 15% by weight, such as 1 to 10% by weight, for example about 2% by weight or about 5% by weight.

d) Fruit Acid and/or Salt Thereof

Compositions according to the invention can also comprise d) 0.01 to 3% by weight of at least one fruit acid and/or a salt thereof. Suitable fruit acids are selected from citric acid, malic acid, lactic acid, mandelic acid, tartaric acid, gluconic acid, fumaric acid and succinic acid, where sodium gluconate and citric acid is particularly preferred as component d). Here, preferred quantitative ranges of component d) are 0.02 to 2% by weight, preferably 0.05 to 1.0% by weight, more preferably 0.08 to 0.5% by weight, in particular 0.1 to 0.3% by weight, such as about 0.1% by weight.

e) Aroma and/or Sweetener

Compositions according to the invention can also comprise e) 0.025 to 10% by weight of aroma and/or sweetener. Suitable sweeteners are selected from alitame, sucralose, aspartame, dulcin, neohesperidin DC, stevioside, suosan and thaumatin. Neohesperidin DC (neohesperidin dihydrochalcone; 1-(4-((2-O-[6-deoxy-α-L-mannopyranosyl]-β-D-glucopyranosyl)oxy)-2,6-dihydroxyphenyl)-3-[3-hydroxy-4-methoxyphenyl]-1-propanone) is a compound with the following formula

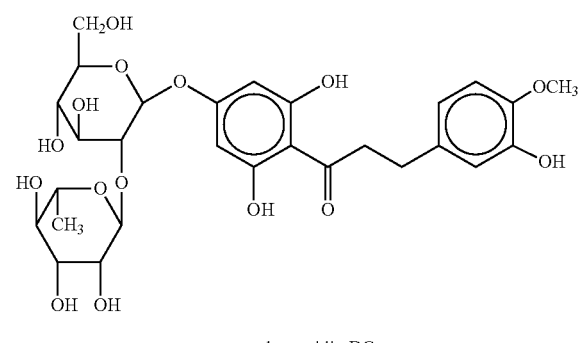

neohesperidin DC

Particularly preferred sweeteners are sucralose, aspartame and/or neohesperidin DC. Preferred amounts of component e) are 0.05 to 5% by weight, preferably 0.1 to 3% by weight, more preferably 0.2 to 2% by weight, in particular 0.5 to 1% by weight, such as about 0.8% by weight.

Preferred weight ratios are
component a): aroma—from 1:100 to 50:1, preferably 1:10 to 2:1;
component a): sweetener—1:200 to 5000:1, preferably 1:10 to 10:1;
aroma: sweetener—1:20 to 1000:1, preferably 1:10 to 100:1.

Preference is given to aromas which conceal or mask the bitter taste of the bispyridinium alkane and are well accepted by the user.

f) Acid, Base and/or Buffer

Compositions according to the invention can also comprise acid, base and/or buffer for adjusting the pH and/or the tonicity.

In a further embodiment, component f) is present in an amount which adjusts the pH to 2 to 8, preferably 4 to 7, more preferably 5 to 6.5, such as 5.5 to 6.0.

In a further embodiment, component f) is present in an amount which adjusts the tonicity to values of preferably 250 to 360 mosmol/kg, more preferably from 270 to 310 mosmol/kg.

Since compositions according to the invention are present as aqueous solutions preferably with a high water content of at least 50% by weight, more preferably of at least 60% by weight, in particular at least 70% by weight, such as at least 80% by weight, for example at least 90% by weight, e.g. at least 94% by weight, of water, they are typically single-phase and clear.

According to the invention, the presence of various ingredients has proven not to be necessary or even disadvantageous. Consequently, in preferred embodiments of the invention, these ingredients are present in a small amount (such as less than 2% by weight and preferably less than 1% by weight) and in particular are not present:

Preferably, compositions according to the invention are free from quaternary ammonium compound, as is obligatorily prescribed according to US 2005/0 169 852 A1. In contrast to the bispyridinium alkanes present according to the invention, the conventional quaternary ammonium compounds such as, for example, cetylpyridinium chloride and benzalkonium chloride, lead to undesired severe foam development upon gargling.

Preferably, compositions according to the invention are free from aromatic alcohol. Within the context of the invention, aromatic alcohols such as benzyl alcohol and phenoxyethanol can form destabilizing products or intermediates such as active oxygen compounds (e.g. peroxides) and aldehydes. Phenoxyethanol also has a negative, furry taste.

Preferred compositions according to the invention are free from hydrogen peroxide or peroxide-releasing compounds, as are obligatorily prescribed according to EP 0 252 278 A2. Disadvantages of peroxides are poor mucosa compatibility and limited stability in the formulation.

Compositions according to the invention are also preferably free from betaine and/or amine oxide, two active compound classes which are proposed according to U.S. Pat. No. 4,420,484 A1. Standard commercial betaines, such as, for example, cocoamidopropylbetaine, lead to undesirably severe foaming of aqueous compositions. In addition, it is assumed that the presence of amine oxides is accompanied by the appearance of nitrosamines, which are known to be carcinogenic and are therefore unacceptable.

Compositions according to the invention are also preferably free from aldehydes as are obligatorily prescribed according to DE 42 01 391. Aldehydes are toxicologically unacceptable.

Preferred preparations according to the invention are also free from silicone oils. Silicone oils typically have low water solubility and their presence thus impedes or prevents the production of the preferred single-phase composition.

Preferred compositions according to the invention have a content of fatty alcohol of less than 10% by weight, such as less than 5% by weight, in particular less than 3% by weight, for example less than 1% by weight. In a particularly preferred embodiment, no fatty alcohol is present.

Particular preference is given to a composition which comprises:
a) 0.1 to 5.0% by weight,
more preferably 0.2 to 3.0% by weight,
in particular 0.5 to 2.0% by weight,
such as about 1.0% by weight, of octenidine,
b) 0.001 to 0.1% by weight,
more preferably 0.002 to 0.05% by weight,
in particular 0.005 to 0.04% by weight,
of stabilizer selected from α-tocopherol and BHT and
c) 0.5 to 30% by weight,
more preferably 1.0 to 20% by weight,
in particular 2.0 to 10% by weight,
such as about 5.0% by weight, of ethoxylated fatty acid monoglyceride, or in particular fatty alcohol alkoxylate
and preferably consists of said components a) to c) and water as the remainder.

Preference is also given to an aqueous-based composition in the form of a mouthwash solution which comprises
a) 0.01 to 1.0% by weight,
more preferably 0.02 to 0.5% by weight,
in particular 0.05 to 0.2% by weight,
such as about 0.1% by weight, of octenidine,
b) 0.01 to 1.0% by weight,
more preferably 0.02 to 0.2% by weight,
in particular 0.03 to 0.1% by weight,
such as about 0.05% by weight, of α-tocopherol,
c) 0.2 to 20% by weight,
more preferably 0.5 to 10% by weight,
in particular 1.0 to 5.0% by weight,
such as about 2.0% by weight, of fatty alcohol ethoxylate, or in particular ethoxylated fatty alcohol monoglyceride,
d) 0.05 to 5.0% by weight,
more preferably 0.1 to 2.0% by weight,
in particular 0.2 to 1.0% by weight,
such as about 0.5% by weight, of fatty acid (salt)
e) 0.08 to 8.0% by weight,
more preferably 0.2 to 5.0% by weight,
in particular 0.5 to 2.0% by weight,
such as about 0.8% by weight, of aroma and/or sweetener and
f) 0.05 to 5.0% by weight,
more preferably 0.1 to 2.0% by weight,
in particular 0.2 to 1.0% by weight,
such as about 0.5% by weight, of polyol such as glycerol
and preferably consists of said components a) to e) and f), and water as the remainder.

Moreover, preference is given to a composition in the form of a ready-to-use product which comprises
a) 0.01 to 0.1% by weight of octenidine,
b) 0.001 to 0.004% by weight of α-tocopherol and/or BHT and
c) about 0.5% by weight of fatty alcohol alkoxylate such as Brij 35
and is optionally isotonically adjusted by adding sodium chloride.

Moreover, the invention relates to the use of the antimicrobially effective composition (or of its components a) and b) and optionally c), d), e) and/or f)) as mouthwash solution or oral antiseptic or for producing a mouthwash solution or an oral antiseptic. A further preferred field of use is general skin, mucosa and wound antisepsis. Mouth antisepsis is one example of a field of use for mucosa antisepsis. The most important indications are:
antimicrobial mouthwashing before dental interventions and jaw surgery interventions;
prophylaxis and therapy of chemotherapy or radiotherapy-induced mucositis;
improvement in oral cavity hygiene in immuno-suppressed patients;
antimicrobial mouthwashing following accidental intake of infectious material into the oral cavity;
before and possibly after operative interventions;
antimicrobial oral care in the case of jaw fractures with intermaxillary immobilization;
root canal antisepsis;
caries and parodontosis treatment;
implantology;
additional mouthwashing for daily routine oral hygiene in particular patient groups (e.g. immunosuppression);
reduction of plaque formation and gingivitis prophylaxis in patients whose teeth cannot be cleaned manually;
before and during dental treatment for reducing the microbial count in aerosols;
prevention or reduction of bacteraemia in patients at risk (e.g. endocarditis prophylaxis);
prevention of infections in intensive-care patients;
prevention of infections in patients under artificial respiration;
before intraoral injections and
treatment of carriers of multiresistant microorganisms in the oral cavity (e.g. MRSA).

In particular, the invention relates to the use of the composition for producing microbicidally effective cosmetic and pharmaceutical preparations and also for producing microbicidally finished articles such as medicinal products and biocidal products such as disinfectants and antimicrobial cleaners. The composition can be used as raw material, concentrate or ready-to-use product for the aforementioned applications. Specifically, the invention also relates to the use of the aforementioned components a) and b), and optionally c), d), e) and/or f) for producing a mouthwash solution and an oral antiseptic, in particular for controlling MRSA and/or $E.\ faecalis$.

All indications can be used with a mouthwash solution and/or an oral antiseptic containing octenidine. Preference is given to treatment in the case of infection with multiresistant pathogens, such as, for example, MRSA (methicillin resistant $S.\ aureus$) and the treatment of paradontitis and of the root canal. Comparisons of the efficacy against the organism $E.\ faecalis$ important in root canal infection show that the formulation preferred according to the invention works significantly better than the commercial product Chlorhexamed Forte®.

The invention also relates to the use of the aforementioned stabilizers for reducing or preventing the decomposition of bispyridinium alkane and in particular a combination of a) bispyridinium alkane and c) auxiliary, in particular for reducing or preventing the formation of degradation products of bispyridinium alkane, of peroxides and/or aldehydes. In this aspect of the invention relating to the stabilization of bispyridinium alkane and in particular the stabilization of a combination of a) bispyridinium alkane and c) auxiliary, suitable stabilizers are also sucralose, Ringer's solution and alkali metal chlorides such as isotonic sodium chloride solution.

The advantages of the invention are evident in particular from the following examples.

EXAMPLES

Unless stated otherwise, data in % by weight.
Methods
Peroxide—Determination

The peroxide content is determined using test rods, Merck No. 10011.0001. At the test rods, peroxidase converts peroxide oxygen to an organic redox indicator and a blue oxidation product is formed. The peroxide concentration is then semi-quantitatively determined by visual assessment of the reaction zone of the analytical rod using the fields of a colour scale. The graduations of the colour scale are 0.5-2-5-10-25 mg/l. Since these concentrations are too low in the course of the experiment, the following peroxide quick test is additionally used: Merck No.: 1.10081.1. The measurement range is 1-3-10-30-100 mg/l peroxide.
Aldehyde—Determination The aldehyde content is likewise determined using test rods, Merck No.: 1.10036.0001. With 4-amino-3-hydrazine-5-mercapto-1,2,4-triazole, formaldehyde forms a purple-red tetrazine. The formaldehyde concentration is determined semiquantitatively by visually comparing the reaction zone of the test rod with the fields of a colour scale. The graduations of the colour scale are 10-20-40-60-100 mg/l.

Octenidine—Determination

The octenidine content is determined by means of liquid chromatography.

Here, following work-up on an RP18 phase, the octenidine is chromatographed and detected in the UV region with the help of a photodiode array detector. The identification is made both via the retention time and also via the specific UV spectrum. A quantification takes place by adding an internal standard.

Formulations and Stability

Example 1

|  | A** | B | C | D | E | F | G | H |
|---|---|---|---|---|---|---|---|---|
| Octenidine | 1.00 | 1.00 | 1.00 | 1.00 | 1.00 | 1.00 | 1.00 | 1.00 |
| Brij 35 | 5.00 | 5.00 | 5.00 | 5.00 | 5.00 | 5.00 | 5.00 | 5.00 |
| α-Tocopherol | — | 0.01 | 0.02 | — | — | — | — | — |
| BHT | — | — | — | 0.005 | 0.01 | 0.02 | 0.04 | — |
| Tocopherol acetate | — | — | — | — | — | — | — | 0.1 |
| BHA | — | — | — | — | — | — | — | — |
| Dodecyl gallate | — | — | — | — | — | — | — | — |
| Ascorbic acid | — | — | — | — | — | — | — | — |
| Demineralized water | ad 100 | ad 100 | ad 100 | ad 100 | ad 100 | ad 100 | ad 100 | ad 100 |
| Zero value | | | | | | | | |
| Octenidine in % | 0.952 | 1.02 | 1.01 | 0.944 | 0.936 | 0.945 | 0.94 | 0.947 |
| Peroxide in ppm | 0 | 0 | 0 | 0 | 0 | 0 | 0 | 0 |
| Aldehydes in ppm | 20 | 10-20 | 10-20 | 20 | 20 | 20 | 10-20 | 20 |
| 6 months +40° C. | | | | | | | | |
| Octenidine in % | 0.921* | 1.00 | 1 | 0.942 | 0.949 | 0.940 | 0.954 | 0.944 |
| Peroxide in ppm | 25-30 | 0 | 0 | 0 | 0 | 0 | 0 | 0.5-2 |
| Aldehydes in ppm | 20-40 | 10-20 | 10-20 | 10-20 | 10-20 | 10-20 | 10-20 | 10-20 |

|  | I | J | K | L | M | N | O | P |
|---|---|---|---|---|---|---|---|---|
| Octenidine | 1.00 | 1.00 | 1.00 | 1.00 | 1.00 | 1.00 | 1.00 | 1.00 |
| Brij 35 | 5.00 | 5.00 | 5.00 | 5.00 | 5.00 | 5.00 | 5.00 | 5.00 |
| α-Tocopherol | — | — | — | — | — | — | — | — |
| BHT | — | — | — | — | — | — | — | — |
| Tocopherol acetate | — | — | — | — | — | — | — | — |
| BHA | 0.01 | 0.02 | — | — | — | — | — | — |
| Dodecyl gallate | — | — | 0.01 | 0.02 | 0.04 | — | — | — |
| Ascorbic acid | — | — | — | — | — | 0.02 | 0.05 | 0.1 |
| Demineralized water | ad 100 | ad 100 | ad 100 | ad 100 | ad 100 | ad 100 | ad 100 | ad 100 |
| Zero value | | | | | | | | |
| Octenidine in % | 0.948 | 0.943 | 0.99 | 1.02 | 1.01 | 0.95 | 0.98 | 1.01 |
| Peroxide in ppm | 0 | 0 | 0 | 0 | 0 | 0 | 0 | 0 |
| Aldehydes in ppm | 20 | 20 | 20 | 20 | 20 | 20-40 | 20-40 | 20-40 |
| 6 months +40° C. | | | | | | | | |
| Octenidine in % | 0.950 | 0.944 | 0.988 | 0.996 | 0.993 | 0.930 | 0.967 | 0.989 |
| Peroxide in ppm | 0 | 0 | 0-0.5 | 0-0.5 | 0 | 0.5 | 0 | 0 |
| Aldehydes in ppm | 10-20 | 10-20 | 10 | 10 | 10 | 40 | 60 | 60-100 |

*= additional peaks in the HPLC analysis.
**= comparison

Preparation of A: combine everything and stir to give a clear solution.

Preparation of B and C: combine octenidine, Brij 35 and water, stir to give a clear solution. Then add alpha-tocopherol and dissolve.

Preparation of D-P: the Brij 35 is firstly melted and the respective stabilizers are stirred in. Water is then added, finally the octenidine. The solution is stirred until clear.

Example 2

|  | Sequence | Q | R | S** |
|---|---|---|---|---|
| Purified water | 9 | 96.05 | 96.00 | 96.10 |
| Octenidine | 1 | 0.10 | 0.10 | 0.10 |
| Macrogol glycerol hydroxystearate 40 EO (Emulgin HRE 40 PH) | 2 | 2.00 | 2.00 | 2.00 |
| Glycerol 85% | 8 | 0.50 | 0.50 | 0.50 |
| Sodium gluconate | 5 | 0.40 | 0.40 | 0.40 |
| Aroma (mint) | 7 | 0.50 | 0.50 | 0.50 |
| DL-α-tocopherol | 3 | 0.05 | 0.10 | — |
| Aspartame | 6 | 0.30 | 0.30 | 0.30 |
| Citric acid monohydrate | 4 | 0.10 | 0.10 | 0.10 |
| Content determination of octenidine in %: zero value |  | 0.099 | 0.099 | 0.099 |
| Content determination of octenidine in %: stability test 6 months at 40° C. |  | 0.102 | 0.101 | 0.094* |
| Content of peroxides in ppm: zero value |  | 0 | 0 | 0.5 |
| Content of peroxides in ppm: stability test 6 months at 40° C. |  | 0 | 0 | 0.5 |
| Content of aldehydes in ppm: zero value |  | 10 | 10 | 10 |
| Content of aldehydes in ppm: stability test 6 months at 40° C. |  | 0 | 0 | 40 |

*= additional peaks in the HPLC analysis
**= comparison

Preparation procedure (Examples Q to S): Purified water is initially introduced and, with stirring, octenidine, glycerol 85% and sodium gluconate are added and stirred until completely dissolved. A separate presolution is prepared from the macrogol glycerol hydroxystearate 40 EO and the aroma and also the tocopherol. The presolution is likewise added with stirring and stirred until completely dissolved. Then, with stirring, the aspartame and citric acid monohydrate are added and stirred until completely dissolved.

Example 3

|  | T** | U | V | W | X |
|---|---|---|---|---|---|
| BHT | — | 0.005 | 0.01 | 0.02 | 0.04 |
| Octenidine | 1.00 | 1.00 | 1.00 | 1.00 | 1.00 |
| Brij 35 | 5.00 | 5.00 | 5.00 | 5.00 | 5.00 |

|  | T** | U | V | W | X |
|---|---|---|---|---|---|
| *Zero value* | | | | | |
| Octenidine in % | 0.952 | 0.944 | 0.936 | 0.945 | 0.940 |
| Peroxide in ppm | 0 | 0 | 0 | 0 | 0 |
| Aldehydes in pppm | 20 | 20 | 20 | 20 | 10-20 |
| *3 months +40° C.* | | | | | |
| Octenidine in % | 0.942 | 0.959 | 0.932 | 0.948 | 0.963 |
| Peroxide in ppm | 0 | 0 | 0 | 0 | 0 |
| Aldehydes in pppm | 20 | 15-20 | 15-20 | 15-20 | 15-20 |
| Appearance of the solution | clear | clear | clear | clear | clear |
| *3 months +60° C.* | | | | | |
| Octenidine in % | 0.819* | 0.946 | 0.945 | 0.939 | 0.944 |
| Peroxide in ppm | 10 | 0 | 0 | 0 | 0 |
| Aldehydes in pppm | 50 | 10-20 | 20 | 10-20 | 20 |
| Appearance of the solution | clear | clear | clear | clear | clear |

*= additional peaks in the HPLC analysis
**= comparison

The invention claimed is:

1. An aqueous-based composition comprising
   a) 0.01% to 20% by weight of octenidine dihydrochloride,
   b) 0.0001% to 2.0% by weight of α-tocopherol,
   c) 0.01% to 20% by weight of macrogol lauryl ether 20-23
   d) at least 50% by weight of water.

2. The composition according to claim 1, wherein the amount of component b) is 0.001 to 1% by weight.

3. The composition according to claim 1, further comprising at least one additive selected from the group consisting of:
   fruit acid and/or salt thereof,
   aroma and/or sweetener, and
   acid, base and/or buffer.

4. A mouthwash solution comprising the composition of claim 1.

5. A method controlling MRSA and/or *E. faecalis* in a subject, comprising administering to a subject in need thereof, a mouthwash solution or an oral antiseptic comprising an effective amount of the composition of claim 1.

6. A method for reducing or preventing the formation of degradation products of octenidine dihydrochloride in an aqueous-based composition comprising:
   0.0001% to 2.0% by weight of α-tocopherol to an aqueous-based composition comprising
   (i) octenidine dihydrochloride, and
   (ii) macrogol lauryl ether 20-23
   to obtain an aqueous-based composition according to claim 1.

* * * * *

UNITED STATES PATENT AND TRADEMARK OFFICE
CERTIFICATE OF CORRECTION

PATENT NO. : 8,609,697 B2  Page 1 of 1
APPLICATION NO. : 12/919523
DATED : December 17, 2013
INVENTOR(S) : Beilfuss et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 246 days.

Signed and Sealed this
Twenty-second Day of September, 2015

Michelle K. Lee
*Director of the United States Patent and Trademark Office*